United States Patent [19]

Mahoney et al.

[11] Patent Number: 4,650,530

[45] Date of Patent: Mar. 17, 1987

[54] APPARATUS AND METHOD FOR FOLDING, BONDING AND SEVERING A WEB

[75] Inventors: Brian J. Mahoney, Outagamie County; William M. Lynch, Winnebago County, both of Wis.

[73] Assignee: Kimberly-Clark Corporation, Neenah, Wis.

[21] Appl. No.: 837,971

[22] Filed: Mar. 10, 1986

[51] Int. Cl.[4] .............................................. B32B 31/00
[52] U.S. Cl. ..................... 156/73.1; 156/200; 156/204; 156/292; 156/461; 156/465; 156/580.1; 493/194; 493/205; 493/208; 493/254; 493/422; 493/425
[58] Field of Search ............... 156/200, 204, 461, 463, 156/465, 290, 292; 493/254, 425, 360, 405, 422, 231, 359, 194, 205, 208; 53/455, 562

[56] References Cited

U.S. PATENT DOCUMENTS

| | | | |
|---|---|---|---|
| 1,612,614 | 12/1926 | Collins | 156/465 X |
| 2,265,075 | 12/1941 | Knuetter | 53/562 X |
| 3,202,066 | 8/1965 | Palmer | 493/434 |
| 3,319,539 | 5/1967 | Johnson et al. | 156/461 X |
| 3,378,429 | 4/1968 | Obeda | 156/515 |
| 3,445,897 | 5/1969 | Franz | 156/204 |
| 3,545,171 | 12/1970 | Salomon | 53/562 |
| 3,618,478 | 11/1971 | Piazze | 493/203 |
| 3,681,176 | 8/1972 | Reifenhauser et al. | 156/515 X |
| 3,751,323 | 8/1973 | Cowen | 156/200 X |
| 3,960,646 | 6/1976 | Wiedamann | 156/518 |
| 4,041,849 | 8/1977 | Tsukasaki | 493/442 X |

Primary Examiner—David Simmons
Attorney, Agent, or Firm—Douglas L. Miller; Donald L. Traut; Jeremiah J. Duggan

[57] ABSTRACT

Apparatus for folding, bonding and severing a longitudinally extending web, comprising a rotatable disc having a plurality of circumferentially spaced-apart, radially extending protrusions at its periphery, means for rotating the disc, means for feeding the longitudinally extending web onto the disc during rotation thereof, so that outer extremities of the protrusions contact the web at its medial region to cause folding of the web so that its sides overlap one another between the protrusions, means for bonding the folded web at its overlapping sides between adjacent protrusions during rotation of the disc, and means for severing the folded web at its overlapping sides between adjacent protrusions during rotation of the disc. Also disclosed is a corresponding method wherein the longitudinally extending web is folded, bonded and severed. The system of the present invention facilitate carrying out of the folding, bonding and severing operations in a single work station and is suitable for use in commercial high-speed operations.

22 Claims, 9 Drawing Figures

APPARATUS AND METHOD FOR FOLDING, BONDING AND SEVERING A WEB

BACKGROUND OF THE INVENTION

1. Field of the Invention

This invention generally relates to an apparatus and process for folding, bonding and severing of web materials, wherein the respective process steps may be carried out in a compact apparatus system, suitable for use in high-speed commercial operations.

2. Description of the Related Art

U.S. Pat. No. 4,041,849 to Y. Tsukasaki discloses a system for folding carton sheet wherein the carton blank is translated along two parallel rails past a plurality of grooved folding rollers rotatably mounted in spaced locations along the rails. The rollers each have top flange portions, which abut the top surface of the folded container blank supported on the rails, and downwardly depending side portions which are progressively, increasingly inclined toward the container blank along its travel path. In such manner the rollers gradually fold the channel portion of the container blank back to form a flattened parallelogram shape. This patent in FIG. 14 shows a means for folding thick cardboard blanks substantially at a 180° angle to the central panel thereof, comprising a pair of pressing discs. Each disc in the pair is arranged at a 45° orientation to the top panel of the carton and opposedly faces the other disc, one having a convex outer periphery and the other having a concave outer periphery, to fold the carton blank without breakage.

U.S. Pat. No. 3,681,175 to H. Reifenhauser discloses an apparatus for ultrasonic welding and cutting of juxtaposed synthetic resin sheets, comprising a sonotrode and an anvil, engageable with each other upon relative movement toward one another. The anvil or sonotrode features a ridge-shaped spacer element running along the middle of its welding face, the spacer element having a height that is slightly less than the combined thickness of the juxtaposed sheets, so that when the spacer element engages the opposite welding face it cuts the sheet's welded surfaces.

U.S. Pat No. 3,378,429 to E. G. Obeda discloses a system for ultrasonically sealing and slitting synthetic fiber textile materials, wherein an ultrasonically activated tool has a first surface for sealing the material and a second surface adjacent thereto for severing the material along its sealed portion, to accomplish sealing and cutting in a single pass as the material is fed between the tool and an opposing anvil.

Other systems for simultaneous cutting and sealing of materials are disclosed in U.S. Pat. No. 4,491,491 to W. Stumpf and U.S. Pat. No. 4,500,372 to S. Mion.

U.S. Pat. No. 3,202,066 discloses a system for folding synthetic plastic sheet stock, comprising a circular blade member with a blade edge on its periphery, and a circular die pad member with resilient, rubber-like material on its periphery. Plastic sheet stock is passed between the blade and the die pad members as they rotate in opposite directions so that the blade edge of the blade member depresses the plastic stock into the rubber-like material of the die pad to cause the rubber-like material to flow and fold the stock about the blade edge.

West German Offenlegungsschrift 2146013 discloses an apparatus for forming a longitudinal fold in a continuous paper web. The paper enters a guiding zone where an upwardly directed air stream from a blower induces upward movement on respective halves of the paper as the paper enters the folding zone. A rotary disc-shaped blade cooperating with a corresponding concave surface circumferentially extending around the periphery of a shaft, with the periphery of the blade disposed therein induces the fold while external bosses rotate to reinforce the folding action. The paper web in passing across the juncture of the blade and notched shaft becomes partially folded, following which the paper is passed to a further folding station wherein air is directed at the partially upwardly folded halves of the paper to complete the initial folding prior to entry into a final folding zone wherein two vertical continuous belts complete the folding action and carry the folded paper away.

SUMMARY OF THE INVENTION

In one aspect, the present invention relates to an apparatus for folding, bonding and severing a longitudinally extending web, comprising a rotatable disc having a plurality of circumferentially spaced-apart, radially extending protrusions at its periphery, means for rotating the disc, means for feeding the longitudinally extending web onto the disc during rotation thereof, so that outer extremities of the protrusions contact the web at its medial region to cause folding of the web so that its sides overlap one another between the protrusions, means for bonding the folded web at its overlapping sides between adjacent protrusions during rotation of the disc, and means for severing the folded web at its lapping overlying sides between adjacent protrusions during rotation of the disc.

In another aspect, the present invention relates to apparatus of the above-described type wherein the bonding means comprise an anvil and an ultrasonic horn each having an ultrasonic bonding surface and positioned on opposite sides of the disc, with means for reciprocating movement between an engaged position wherein the bonding surfaces face one another in contact with outer surfaces of the folded web and a disengaged position in spaced relationship thereto and means for energizing the ultrasonic horn while the bonding surfaces are in the engaged position.

Another aspect of the invention relates to a method for folding, bonding and severing a longitudinally extending web, comprising providing a rotatable disc having a plurality of circumferentially spaced-apart, radially extending protrusions at its periphery, rotating the disc, feeding the longitudinally extending web onto the disc during rotation thereof, so that outer extremities of the protrusions contact the web at its medial region to cause folding of the web so that its sides overlap one another between the protrusions, bonding the folded web at its overlapping sides between adjacent protrusions during rotation of the disc, and severing the folded web at its overlapping sides between adjacent protrusions during rotation of the disc.

Another aspect of the invention relates to a method of the above-described type, wherein the bonding and severing steps are carried out contemporaneously.

Other aspects and features of the present invention will be apparent from the ensuing disclosure and appended claims.

DETAILED DESCRIPTION OF THE PREFERRED EMBODIMENTS

As indicated, the prior art has disclosed the provision of various apparatus and processes for folding of materials, and for materials bonding and severing. Additionally, the prior art, as described hereinabove, has taught to simultaneously carry out the bonding and severing operations by means of unitary apparatus in an effort to provide a more compact process system, which is simpler in construction by virtue of eliminating transfer and conveying means between adjacent work stations therein. Nonetheless, the prior art has not developed a satisfactory process system for carrying out the folding, bonding and severing operations in a unitary work station.

The provision of such unitary work station for conducting folding, bonding and severing operations is highly advantageous in the processing of longitudinally extending webs to form discrete product articles. An example is the manufacture of disposable garments such as training pants, formed from a longitudinally extending web by longitudinally folding the web, bonding it at longitudinally spaced-apart intervals, and severing the sequential bonded areas to form discrete severed garment articles with side seams derived from the bonded areas. The prior art, as indicated, has not provided a suitable system for manufacturing such garments wherein folding, bonding and severing are carried out in unitary work station. Accordingly, the present invention represents a significant advance in the art in the provision of such a system, which may be configured to occupy a comparatively small space in the overall manufacturing plant, thereby avoiding the necessity for complex and costly material conveyance and transfer means, as otherwise associated with the provision of a multiplicity of work stations for carrying out these respective process steps.

Figure 1:
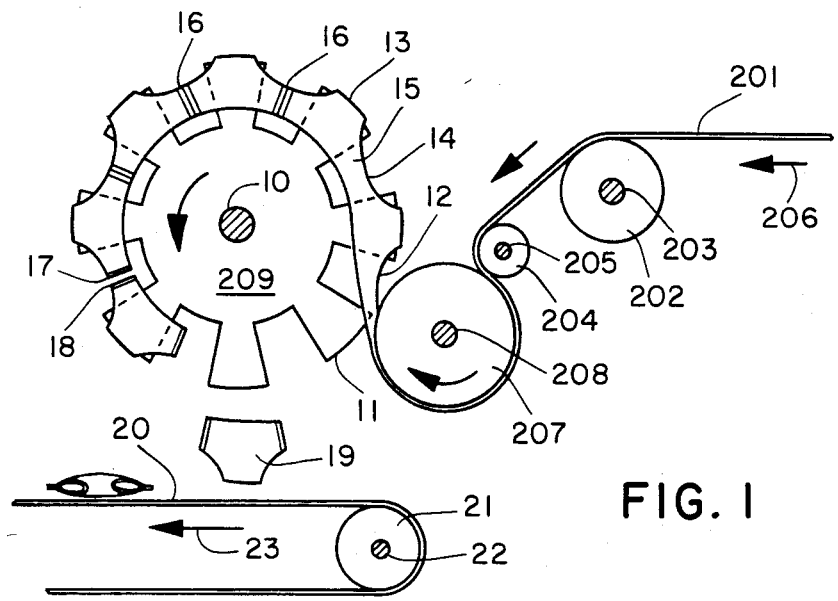
FIG. 1 is a schematic elevational view of a simplified process system according to one embodiment of the present invention.

FIG. 1 illustrates a simplified version of one embodiment of the present invention, for the production of pant-type garments from a longitudinally extending web. The longitudinally extending web 201 enters the system as shown, being translated in the direction of the arrow 206 onto the upper cylindrical surface of guide roll 202 mounted on shaft 203 for rotation, from which the web contacts transfer roll 204 mounted on shaft 205 for rotation and is introduced to the outer surface of feed drum 207, mounted for rotation on shaft 208. Feed drum 207 has an outer surface which may be of any suitable configuration, but is advantageously concavely contoured to promote folding of the web, as shown in FIG. 1 by the web portion 12 to be folded, as the web is introduced onto disc 209. Disc 209 is mounted on shaft 10 for rotation and driven by suitable drive means (not shown).

Disc 209 has a plurality of circumferentially spaced-apart radially extending protrusions 11 at its periphery, so that a corresponding series of gaps or notches is provided around the periphery of the disc, between the adjacent protrusions. The protrusions 11 may have any suitable shape, as for example the generally inverted frusto-pyramidal shape shown in FIG. 1 with radially outwardly diverging sides.

As the web passes onto the rotating disc 209 supported web portions 13 repose on the protrusions, with the unsupported web portions 14 lying between adjacent protrusions. The web thus is fed onto the disc during rotation so that outer extremities of the protrusions contact the web at its medial, i.e., central region, to cause folding of the web so that its sides 15 overlap one another between the protrusions, thereby placing the web into suitable folded configuration for subsequent bonding and severing.

Bonding then is carried out along the radial bond regions 16 by suitable bonding means as hereinafter described in greater detail, followed by medially severing the bonded regions of the bonded web to provide bonded and severed edges 17, 18, i.e., the bonded regions have a dimensional extent on either side of the severing line so that the severing produces articles on either side of the cut which have bonded marginal seams.

The resulting bonded and severed folded article then remains disposed on the associated protrusion during rotation of the disc to a point where the product garment article 19 is discharged from the disc by gravitational fall or other means onto an endless belt conveyor 20. The conveyor is mounted on roll 21, which in turn is mounted for rotation on shaft 22, to translate the conveyor in the direction indicated by arrow 23.

Figure 2:
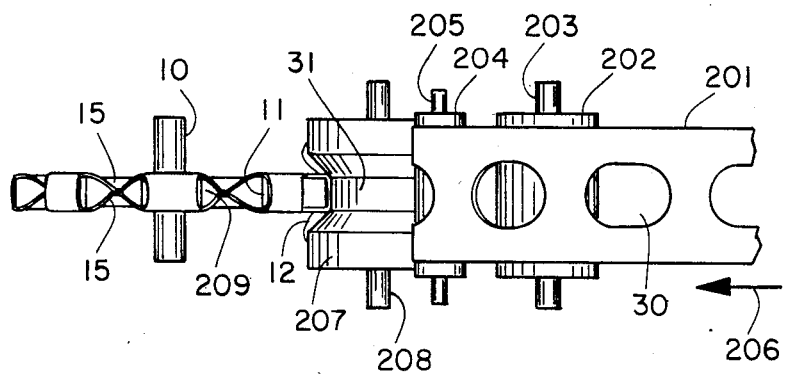
FIG. 2 is a top plan view of the process system of FIG. 1.

FIG. 2 is a plan view of the apparatus shown in FIG. 1 exclusive of the endless belt conveyor 20 and associated elements, which have been deleted for clarity. As shown, the longitudinally extending web 201 has a plurality of longitudinally spaced-apart sequential leg openings 30. Also shown in FIG. 2 is the concavely contoured outer surface 31 of the feed drum 207 which acts to promote folding of the web as the web is fed onto the disc 209 during its rotation. This drawing also shows the overlapping sides 15 of the folded web between the protrusions 11 of the rotatable disc.

Figure 3A:
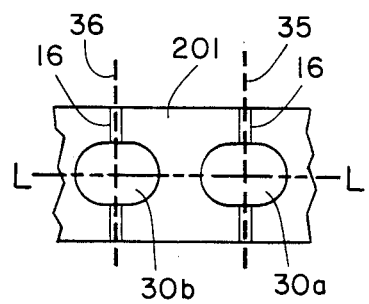
FIGS. 3A, 3B and 3C are sequential (time-sequence) elevational views of a portion of a longitudinally extending web, illustrating the folding, bonding and severing steps utilized to produce an undergarment product article according to one embodiment of the present invention.
Figure 3B:
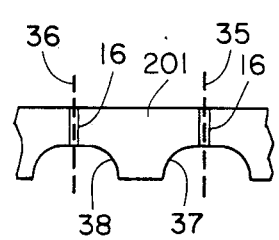
Figure 3C:
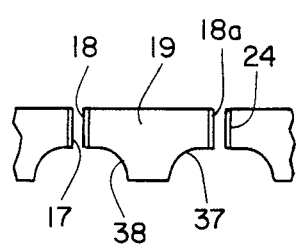

The sequence of folding, bonding and severing operations is illustrated by FIGS. 3A, 3B and 3C with reference to a section of the longitudinally extending web 201. The illustrated web portion has leg openings 30a and 30b therein each of generally circular configuration with their centers positioned along the longitudinal axis L—L of the web. Vertical bonding regions 16 and severing lines 35 and 36, demarcate the location of the bonding and severing steps conducted subsequent to folding of the web. FIG. 3B shows the web portion as folded along the longitudinal center line L—L, so that the circular leg openings 30a and 30b shown in FIG. 3A provide the arcuate cut-outs 37 and 38 on the folded web portion having its sides overlapping one another. The web portion as shown in FIG. 3B is subsequently bonded along the regions 35 and 36 and then severed at intermediate lines 35 and 36 along the bonding region to form the discrete product garment articles 19 as shown in FIG. 3C with the adjacent articles being separated along the bonded and severed edges 17 and 18 so that the product garment article 19 has bonded margins at the edges 18 and 18a, with leg openings boarded by the edged of the arcuate cut-outs 37 and 38. The edges 18a and 24 correspond to the locus of bond line 35, and edges 17 and 18 correspond to the locus of bond line 36, respectively.

Figure 4:
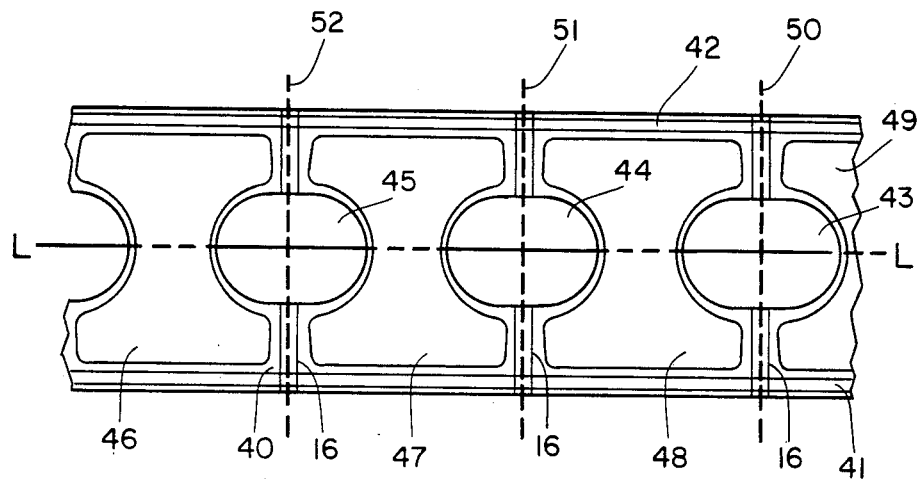
FIG. 4 is a plan view of a longitudinally extending web for the manufacture of undergarment product articles, wherein each product article is provided with an interiorly disposed absorbent body, and with the web marked with the longitudinal fold line L—L, as well as the vertical bonding and severing lines.

FIG. 4 shows an alternative longitudinally extending web construction wherein the web 40 has disposed at its margins elastic ribbons 41 and 42, which serve to elastically gather the waist openings of the garment articles produced from the web. Disposed at regularly spaced intervals along the longitudinal center line L—L of the web are leg openings 43, 44 and 45, which may be generally circular in shape. Between each of the respective leg openings is positioned an hourglass-shaped absorbent body 46, 47, 48 and 49 which in the product garment articles provides an absorbent liner for the articles. For reference, bonding regions 16 and severing lines 50, 51 and 52 are illustrated, with the respective folding, bonding and severing operations being carried out in a similar manner as described in connection with FIGS. 3A, 3B and 3C.

Figure 5:
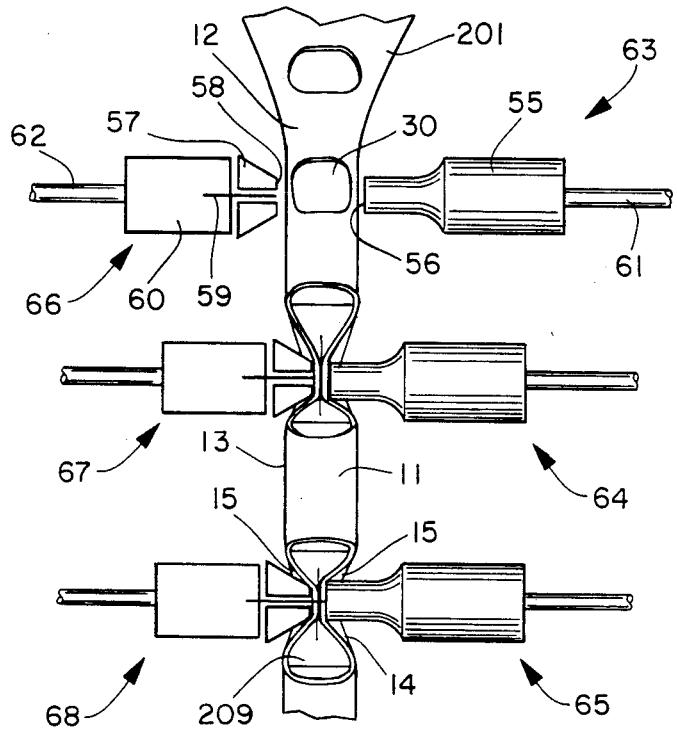
FIG. 5 is a top plan view of the rotatable disc of the FIG. 1 system, additionally showing illustrative bonding and severing means utilizable therewith.

FIG. 5 is a top plan view of a portion of the disc as shown in FIG. 1 wherein the web 201 having spaced-apart leg openings 30 therein is fed as a folding web 12 onto the rotating disc 209. The disc has associated therewith a plurality of bonding and severing means laterally reciprocatable along lines parallel to the axis of rotation of the disc 209. These bonding and severing means may suitably be carried on a carousel from which they come into contact with the folded web at its overlapping sides between adjacent protrusions of the rotating disc.

The ultrasonic bonding horn assemblies 63, 64 and 65 are mounted on shafts for reciprocating movement as more fully described hereinafter. Similarly, anvil and severing assemblies 66, 67 and 68 are mounted on shafts on the opposite side of the rotating disc for corresponding reciprocating movement. The ultrasonic horn assembly 63 comprises an ultrasonic horn 55 having a bonding surface 56. Disposed on the opposite side of the disc in opposed facing relationship to the ultrasonic bonding horn assembly 63 is the anvil and severing assembly 66, comprising anvil 57 having a bonding surface 58. The anvil has a passage therein with an opening at the anvil's bonding surface, and a knife 59 is mounted in the passage. The knife has at its forward end a severing surface proximate the passage opening, and is joined at its opposite end to the actuator 60 for directing the severing surface of the knife means toward the bonding surface 56 of the ultrasonic horn 55 and against the web 201 when the bonding surfaces of the horn and anvil are in their engaged position as shown by horn assemblies 64 and 65, respectively in contact with anvil and severing assemblies 67 and 68. The actuator means 60 subsequent to effecting severing functions shown with respect to assembly 68 retracts the knife into the passage within the anvil. The ultrasonic bonding horn assembly 63 is mounted for reciprocating movement on shaft 61 and the anvil and severing assembly 66 is likewise mounted for reciprocating movement on shaft 62.

The respective horn and anvil assemblies and the severing means assemblies may be mounted on carousels (not shown) on either side of the disc and equipped with means for reciprocating the same between an engaged position corresponding to the assemblies 64/67 and 65/68 wherein the bonding surfaces of the respective assemblies face one another in contact with outer surfaces of the folded web, and a disengaged position in spaced relationship thereto. When the bonding surfaces are in such engaged position, the ultrasonic horns are energized and the actuator functions to direct the severing surface of the knife means toward the bonding surface of the ultrasonic horn and against the web disposed between the respective horn and anvil bonding surfaces to effect severing of the folded web contemporaneously with bonding thereof.

The horn and anvil assemblies may be carried on respective carousels or other frame means rotating a synchrony with the rotating disc 209, so that the horn and anvil assemblies are in the disengaged position when the web is fed onto the rotating disc, and subsequently the horn and anvil assemblies are brought into engagement with one another, so that their bonding surfaces bear against the overlapping sides 15 of the unsupported web portions 14 between the protrusions 11. The respective horn and anvil assemblies may be reciprocated into and away from the engaged position by respective cam arrangements whereby the shafts 61 and 62 function in the manner of push rods, with the end opposite the horn or anvil assembly being in contact with a cam member which is constructed and arranged to urge the horn and anvil assemblies inward into the engaged position at the predetermined point during rotation. Preferably, the horn and anvil bonding surfaces are retained in the engaged position for a predetermined arc length or period of time during rotation of the disc, to ensure accurate and efficient bonding and severing of the folded web. Preferably, the disc is vertically oriented and the direction of reciprocal movement of the horn and anvil assemblies is in a horizontal plane.

Figure 6:
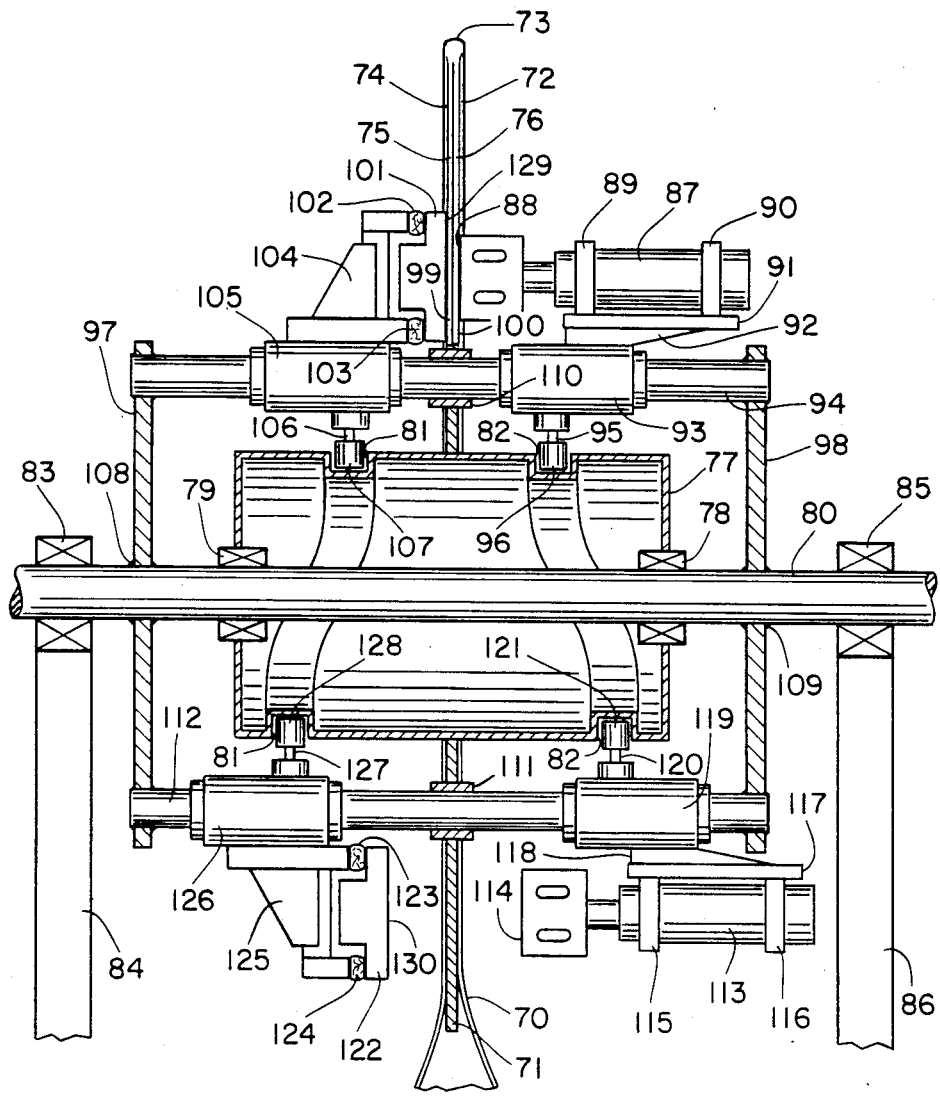
FIG. 6 is a cross-sectional elevational view of an apparatus according to another embodiment of the present invention.

FIG. 6 shows a cross-sectional elevational view of an apparatus according to another embodiment of the present invention. In this construction, disc 70 during its rotation receives the web 71, so that supported web portions 73 repose on protrusions 72 which are provided in circumferentially spaced-apart relationship at the periphery of the disc. The unsupported web portions 74 repose between the adjacent protrusions with the web being folded on the disc to provide overlapping sides 75 and 76 between the protrusions, in the previously described manner. The disc 70 surrounds in its central portion a stationary cam track drum 77. The disc 70 is mounted on shaft 94 which is attached at its ends on end plates 97 and 98, which in turn are mounted to a rotatable shaft 80 at points 108 and 109, respectively. The shaft 94 is joined by a hub 110 to the disc 70 to provide a unitary rotating construction. The drum 77 is in turn mounted via bearings 78 and 79 on the rotatable shaft 80. The shaft 80 is positioned at one end in a journal bearing 83 mounted on support member 84, with the other end of the shaft positioned for support in a journal bearing 85 mounted on support member 86, and joined, either directly or by suitable coupling, to a drive means (not shown), to effect rotation of the shaft 80, plates 97 and 98, shaft 94 and disc 70.

The cam track drum 77 has cam tracks 81 and 82 in its outer cylindrical surface as shown to provide for reciprocating movement of anvil and ultrasonic horn bonding means as described below.

The bonding means comprise an ultrasonic bonder 87 having a bonding surface 88. The bonder 87 is mounted by means of vertical supports 89 and 90 on a base plate 91, in turn joined by flange 92 to cam 93. The cam is mounted for reciprocating movement on shaft 94, and is coupled by means of cam rod 95 to cam follower 96 reposed in the cam track 82. The cam 93 may be provided with an internal assembly of roller bearing or other surface means providing for free movement of the cam along shaft 94 during rotation around the cam track drum 77.

Opposedly positioned with respect to bonder 87 is an anvil 101 having an anvil bonding surface 129. The bonding surfaces 88 and 129 of the ultrasonic bonder 87 and anvil 101, respectively, are illustrated in engaged position with the bonding surfaces facing one another in contact with outer surfaces (overlapping sides 75, 76) of the folded web 71. The ultrasonic bonder 87 may be suitably programmed by cycle timer or other means to energize the ultrasonic horn when the respective horn and anvil bonding surfaces are in the engaged position, to effect ultrasonic bonding of the overlapped plies 99 and 100 of the folded web. The anvil 101 is mounted on resilient gaskets 102 and 103 which assist in the self-aligning positioning of the anvil in the engaged position. The resilient gaskets 102, 103 in turn are mounted on the anvil support frame 104 affixed to cam 105. Cam 105 is mounted on the cam shaft 94 and joined via cam rod 106 to cam follower 107 reposed in the cam track 81.

The lower portion of FIG. 6 shows corresponding ultrasonic horn and anvil assemblies which are in a disengaged position, as is desired for feeding of the web onto the disc and discharging of product articles therefrom. As shown, shaft 112 is mounted on hub 111 in turn mounted to disc 70. The ultrasonic bonder 113 has a bonding surface 114. The bonder 113 is mounted via vertical supports 115 and 116 to base plate 117, in turn coupled by flange 118 to cam 119. The cam 119 is coupled via cam rod 120 to cam follower 121 reposed in cam track 82.

The anvil 122 presenting a bonding surface 130 is mounted on resilient gaskets 123 and 124 disposed on an anvil support frame 125 in turn coupled to cam 126. The cam 126 is joined by cam rod 127 to cam follower 128, reposed in cam track 81.

During rotation of the shaft 80, plates 97 and 98, shaft 94 and disc 70 joined thereto are integrally rotated. In the course of rotation, the cam followers 96, 107, 121 and 128 travel over their associated cam tracks on stationary cam track drum 77 and induce reciprocating movement of the associated horn and anvil bonding means between an engaged position where the horn and anvil bonding surfaces face one another in contact with outer surfaces of the folded web, as shown in the upper portion of FIG. 6 with respect to bonder 87 and anvil 101, and a disengaged position in spaced relationship to the engaged position, the disengaged position corresponding to the lower portion of FIG. 6 in respect of bonder 113 and anvil 122.

Although the FIG. 6 embodiment has been shown as comprising two horn/anvil assemblies, it will be apparent that a greater or lesser number of assemblies may be utilized depending on the specific web material, process system size, operating speed, etc.

In one commercial embodiment corresponding to the apparatus as shown in FIG. 6, the stationary cam track drum 77 may have a length of 32 inches with a diameter distance between shaft 94 and shaft 112 being 26.75 inches, such that the travel of the respective ultrasonic horns and anvils on the cam shafts is each 10 inches. In such embodiment, the axial distance between end plates 97 and 98 is 42.5 inches and the diameter of the disc is 51.75 inches. Such apparatus is suitable for the folding and bonding of a web of multi-ply construction comprising, for example, outer layers of polymer coating and inner layers of liner material.

Although no specific web severing means have been shown in the FIG. 6 diagram for simplicity of illustration and description, it will be appreciated that the anvils 101 and 122 may be provided with a passage therein in which is mounted a knife means, in the manner shown and described for the FIG. 5 embodiment of the present invention.

Figure 7:
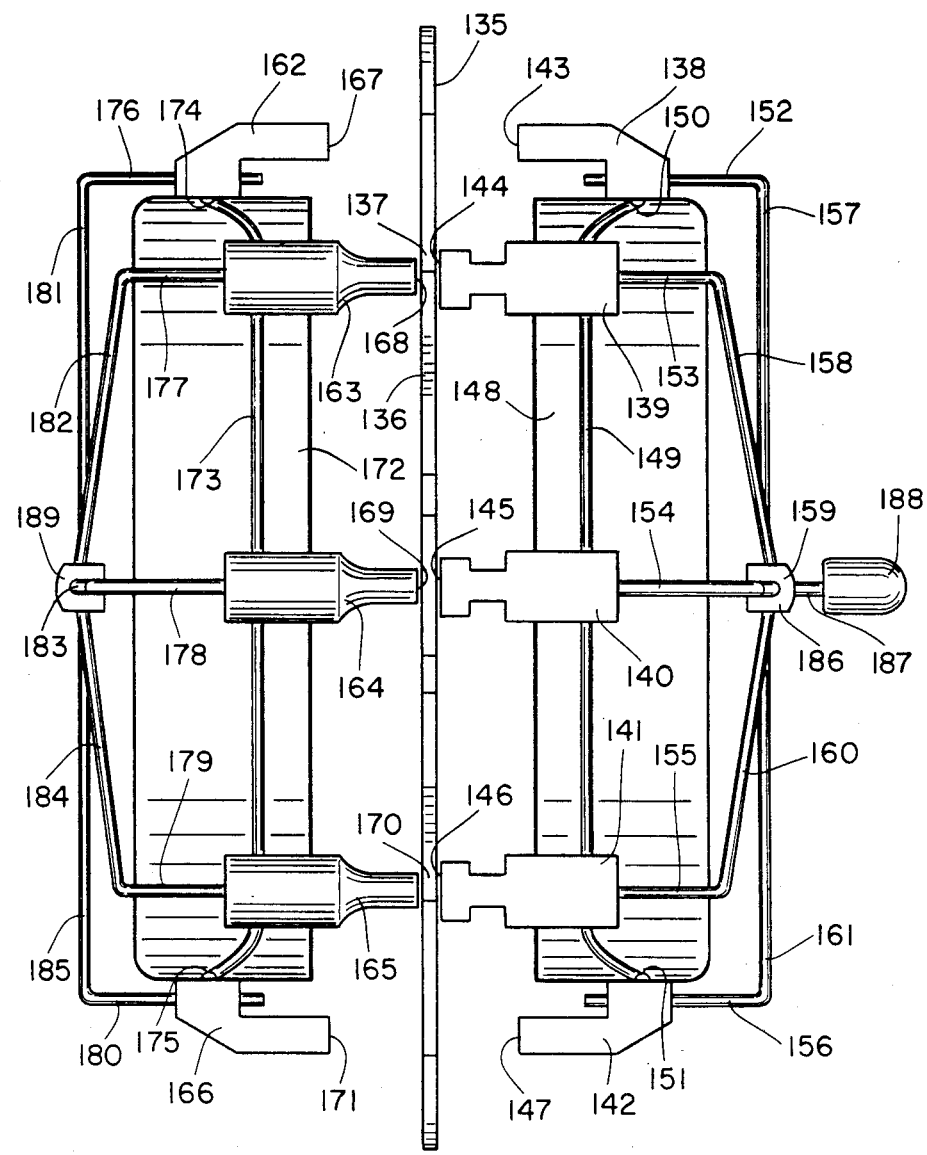
FIG. 7 is an elevational view of still another embodiment according to the present invention.

FIG. 7 shows a folding, bonding and severing apparatus according to another embodiment of the present invention, wherein the web has been omitted for clarity. As shown, the disc 135 has on it periphery a plurality of circumferentially spaced-apart radially extending protrusions 136, providing gaps or spaces 137 therebetween.

A plurality of anvils 138, 139, 140, 141 and 142, with anvil bonding surfaces 143, 144, 145, 146 and 147, respectively, are arranged for sliding movement on respective cam rods 152, 153, 154, 155 and 156. The anvils are mounted on the cam track cylinder 148 having cam track 149 therein in which cam followers, e.g., cam follower 150 of anvil 138 and cam follower 151 of anvil 142, effect reciprocating movement of the anvils so that their bonding surfaces are brought into contact with the overlapping sides of the web (not shown) during the rotation of disc 135. The cam rods 152, 153, 154, 155 and 156 are joined at their rear extremities with spokes 157, 158, 159, 160 and 161, respectively. The spokes are journaled at their opposite ends into hub 186 coupled by a drive shaft 187 to drive motor 188. By such arrangement, the spoke/cam rod assembly is rotated so that the respective anvils follow the cam track 149 in the stationary cam track cylinder 148. Thus, the array of anvils is rotated in synchrony with the rotatable disc 135, such that the anvils are sequentially brought into engaged position with the folded web for bonding and subsequent thereto are retracted to a disengaged position.

In like manner, the ultrasonic bonders 162, 163, 164, 165 and 166 with respective bonding surfaces 167, 168, 169, 170 and 171 are mounted for sliding transverse movement on cam rods 176, 177, 178, 179 and 180. The rods are joined at their opposite ends with spokes 181, 182, 183, 184 and 185, respectively, the spokes being attached to hub 189 joined to drive shaft 187. The ultrasonic bonders (ultrasonic horns) are arranged with cam followers, e.g., cam follower 174 of bonder 162 and cam follower 175 of bonder 166, in the cam track 173 of the (stationary) cam track cylinder 172. The ultrasonic bonders during rotation of the rod-spoke assembly thus are reciprocated between an engaged position wherein the bonding surface of the ultrasonic horn faces the bonding surface of the anvil, both bonding surfaces in contact with respective outer surfaces of the folded web, and a disengaged position in spaced relationship thereto. Cycle timer or other suitable energizing means may suitably be utilized to initiate emission of ultrasonic vibrations at the bonding surfaces of the respective ultrasonic horns, during the arc length or time period that the ultrasonic horn is in the engaged position. The array of ultrasonic horns thus is rotated in synchrony with the rotatable disc 135, so that the bonding surfaces of the horn are maintained in contact with the corresponding bonding surfaces of the anvils during a predetermined arc length of period of time during rotation of the disc.

The apparatus of FIG. 7 utilizes a severing means (not shown) which is coordinated with the bonders to sever the bonded web at a preselected location.

Although the present invention has been described in various embodiments as utilizing ultrasonic bonding for bonding of the folded web, it will be appreciated that other means and methods of bonding may be utilized to advantage in the broad practice of the invention. Such other potentially useful bonding methods include hot-knife sealing, adhesive application, electron beam welding, ultraviolet radiation of webs of UV-curable material to induce thermosetting and bonding at contiguous portions thereof, etc. Further, it will be recognized that in some instances it may be desirable to perform the bonding operation subsequent to the severing operation, as well as to perform the respective folding, bonding and severing steps in other sequences.

Further, although the invention has been shown and described in connection with gravitational fall discharge of product articles from the protrusions of the rotating disc, it will be appreciated that other methods of discharging and/or removal of articles from the disc may be employed, including air blast entrainment removal, mechanical takeoff, etc. In addition, it may be useful in some applications of the present invention to tightly retain the folded web in position on the disc during web processing by vacuum suction, mechanical clamping, etc.

Further, although preferred embodiments of the present invention have been described in detail, it will be appreciated that numerous modifications and variations thereof are possible, together with other embodiments, and accordingly, all such apparent modifications, variants and embodiments are to be regarded as being within the spirit and scope of the present invention.

What is claimed is:

1. Apparatus for folding, bonding and severing a longitudinally extending web, comprising:
    a rotatable disc having a plurality of circumferentially spaced-apart, radially extending protrusions at its periphery;
    means for rotating the disc;
    means for feeding the longitudinally extending web onto the disc during rotation thereof, so that outer extremities of the protrusions contact the web at its medial region to cause folding of the web so that its sides overlap one another between the protrusions;
    means for bonding the folded web at its overlapping sides between adjacent protrusions during rotation of the disc; and
    means for severing the folded web at its overlapping sides between adjacent protrusions during rotation of the disc.

2. Apparatus according to claim 1, wherein said bonding means and said severing means are constructed and arranged to contemporaneously bond and sever the web.

3. Apparatus according to claim 1, wherein the protrusions of the rotatable disc are of generally inverted frusto-pyramidal shape having radially outwardly diverging sides.

4. Apparatus according to claim 1, wherein said bonding means ultrasonically bond the web.

5. Apparatus according to claim 4, wherein the bonding means comprise an anvil and an ultrasonic horn each having an ultrasonic bonding surface and positioned on opposite sides of the disc, with means for reciprocating movement between an engaged position wherein the bonding surfaces are facing one another in contact with outer surfaces of the folded web and a disengaged position in spaced relationship thereto, and means for energizing the ultrasonic horn while the bonding surfaces are in the engaged position.

6. Apparatus according to claim 5, wherein the anvil bonding surface has a passage therein with an opening at the anvil's bonding surface, and a knife is mounted in the passage with its severing surface proximate to the passage opening, the knife being joined to an actuator means for (i) directing the severing surface of the knife toward the ultrasonic horn bonding surface and against the web when the bonding surfaces of the ultrasonic horn and the anvil are in the engaged position, for severing the web and (ii) retracting the knife after severing has been effected.

7. Apparatus according to claim 5, comprising means for retaining the bonding surfaces in the engaged position for a predetermined arc length during rotation of the disc.

8. Apparatus according to claim 5, wherein the direction of the reciprocating movement of the horn and anvil is perpendicular to the plane of the disc.

9. Apparatus according to claim 1, further comprising means for rotating the bonding means and the severing means synchronously with the disc.

10. Apparatus according to claim 1, wherein the feeding means comprise:
    a rotatable drum;
    means for introducing the longitudinally extending web onto the rotatable drum at a first predetermined position thereon;
    means for rotating the rotatable drum, with the rotatable drum disposed proximately to the rotatable disc so that the web is discharged from the rotatable drum at a second predetermined position thereon circumferentially spaced from the first predetermined position, onto the disc.

11. Apparatus according to claim 10, wherein the rotatable drum has a concavely contoured outer surface to initiate folding of the web as the same is discharged from the rotatable drum onto the disc.

12. A method for folding, bonding and severing a longitudinally extending web comprising:
    providing a rotatable disc having a plurality of circumferentially spaced-apart radially extending protrusions at its periphery;
    rotating the disc;
    feeding the longitudinally extending web onto the disc during rotation thereof, so that outer extremities of the protrusions contact the web at its medial region to cause folding of the web so that its sides overlap one another between the protrusions;
    bonding the folded web at its overlapping sides between adjacent protrusions during rotation of the disc; and severing the folded web at its overlapping sides between adjacent protrusions during rotation of the disc.

13. A method according to claim 12, wherein said bonding and severing steps are carried out contemporaneously.

14. A method according to claim 12, wherein the folded web is ultrasonically bonded.

15. A method according to claim 14, comprising providing an anvil and an ultrasonic horn each having an ultrasonic bonding surface, positioning the anvil and ultrasonic horn on opposite sides of the disc, reciprocating each of the anvil and ultrasonic horn between an engaged position wherein the bonding surfaces face one another in contact with outer surfaces of the folded web and a disengaged position in spaced relationship to the engaged position, and energizing the ultrasonic horn while the bonding surfaces are in the engaged position.

16. A method according to claim 15, comprising providing the anvil bonding surface with a passage therein having an opening at the anvil's bonding surface, mounting a knife in the passage with its severing surface proximate to the passage opening, directing the severing surface of the knife toward the ultrasonic horn bonding surface and against the web while the bonding surface of the ultrasonic horn and anvil are in the engaged position, for severing the web, and retracting the knife after severing has been effected.

17. A method according to claim 15, comprising retaining the bonding surfaces in the engaged position for a predetermined arc length during rotation of the disc.

18. A method according to claim 15, comprising retaining the bonding surfaces of the engaged position for a predetermined period of time during rotation of the disc.

19. A method according to claim 15, wherein the direction of the reciprocating movement of the horn and anvil is perpendicular to the plane of the disc.

20. a method according to claim 12, further comprising rotating the bonding means and the severing means synchronously with the disc.

21. A method according to claim 12, wherein said feeding of the longitudinally extending web onto the rotatable disc is carried out by the steps of introducing the longitudinally extending web onto a rotatable drum at a first predetermined position thereon, rotating the rotatable drum, positioning the rotatable drum proximate to the disc and discharging the web from the rotatable drum at a second predetermined position thereon circumferentially spaced-apart from the first predetermined position, onto the disc.

22. A method according to claim 21, wherein the rotatable drum has a concavely contoured outer surface to initiate folding of the web as the web is discharged from the rotatable drum onto the disc.

* * * * *